United States Patent [19]

Ishii

[11] Patent Number: 4,891,460

[45] Date of Patent: Jan. 2, 1990

[54] PROCESS FOR PRODUCING ALKYLIDENENORBORNENES

[75] Inventor: Yasutaka Ishii, Takatsuki, Japan

[73] Assignee: San-Petrochemicals Co., Ltd., Japan

[21] Appl. No.: 707,601

[22] Filed: Mar. 4, 1985

[30] Foreign Application Priority Data

Mar. 9, 1984 [JP] Japan ................................ 59-44929

[51] Int. Cl.$^4$ ............................................... C07C 2/76
[52] U.S. Cl. .................................... 585/360; 585/561; 585/363
[58] Field of Search .................... 585/360, 361, 363

[56] References Cited

U.S. PATENT DOCUMENTS

| | | | |
|---|---|---|---|
| 3,535,395 | 10/1970 | Schneider | 585/363 |
| 3,535,396 | 10/1970 | Schneider | 585/363 |
| 3,538,171 | 11/1970 | Schneider | 585/363 |
| 3,594,433 | 7/1971 | Schneider | 585/363 |
| 3,683,038 | 8/1972 | Schneider | 585/363 |
| 3,683,039 | 8/1972 | Schneider | 585/363 |
| 3,694,517 | 9/1972 | Schneider | 585/363 |
| 3,696,157 | 10/1972 | Schneider | 585/363 |
| 3,728,406 | 4/1973 | Vrinssen et al. | 585/360 |
| 3,776,966 | 12/1973 | Schneider | 585/363 |

Primary Examiner—Asok Pal
Attorney, Agent, or Firm—Ostrolenk, Faber, Gerb & Soffen

[57] ABSTRACT

The present invention provides a process for producing alkylidenenorbornenes by reacting $C_4$–$C_6$ acyclic conjugated dienes with cyclopentadiene, dicyclopentadiene, or a methyl- or dimethyl-substituted derivative thereof in the presence of a catalyst derivative composed of:

(A) a titanium-containing compound, and
(B) at least one metallic reducing agent containing the group IA, IIA or IIIA metals in the periodic table.

20 Claims, No Drawings

PROCESS FOR PRODUCING ALKYLIDENENORBORNENES

BACKGROUND OF THE INVENTION (1) Field of the Invention

The present invention relates to a process for producing directly alkylidenenorbornenes from acyclic conjugated dienes and cyclopentadienes.

(2) Description of the Prior Art

Alkylidenenorbornenes, particularly ethylidenenorbornene [5-ethylidenebicyclo (2. 2. 1) heptene-2 (hereinafter referred to simply as "EBH")] has been industrially produced as a vulcanizing termonomer for ethylene/propylene rubber.

In this connection, almost all processes for the production of EBH which have been heretofore known are those in which isomerization of vinylnorbornene 5-vinylbicyclo (2. 2. 1) heptene-2 (hereinafter referred to simply as "VBH")] is utilized. Such VBH has been produced in accordance with Diels-Alder reaction of butadiene (hereinafter referred to as "BD") and cyclopentadiene (hereinafter referred to as "CPD"). Namely, EBH has been heretofore obtained from BD and CPD according to two-stage reaction.

In this respect, it is advantageous that EBH may be produced directly from BD and CPD, in other words, EBH may be obtained in accordance with one-stage reaction operation which requires no isomerization process. That is to say, in the above-mentioned two-stage reaction, the operation of producing EBH is not only complicated but also cannot avoid the yield of EBH from being lowered due to thermo-rearrangement of VBH. Such disadvantage, however, can be overcome by using the one-stage reaction operation and therefore it is favorable process.

Processes for producing directly EBH from BD and CPD have scarcely been proposed heretofore in spite of the various advantages involved in such direct process as mentioned above. Especially, no report on such direct preparation of EBH in which a titanium-containing compound is used as the catalyst as in the present invention has been made.

SUMMARY OF THE INVENTION

In view of the above, it is an object of the present invention to provide a process for producing directly EBH from BD and CPD with a favorable yield.

Namely, the present invention relates to a process for producing alkylidenenorbornenes by reacting $C_4$–$C_6$ acyclic conjugated dienes with cyclopentadiene, dicyclopentadiene, or a methylsubstituted or dimethyl-substituted derivative thereof characterized in that the reaction is carried out in the presence of a catalyst composed of:

(A) a titanium-containing compound, and
(B) at least one metallic reducing agent containing the group IA, group IIA, or group IIIA metals in the periodic table.

DETAILED DESCRIPTION OF THE INVENTION

Dienes used in the present invention are $C_4$–$C_6$ acyclic conjugated dienes such as BD, isoprene, piperylene and the like.

Cyclopentadienes to be reacted with the aforesaid conjugated dienes are CPD and dicyclopentadiene (hereinafter referred to as "DCPD"). In addition, methylcyclopentadiene, dimethylcyclopentadiene, dimethyldicyclopentadiene and the like which are substituted members of said cyclopentadienes may also be utilized.

Such alkylidenenorbornenes obtained by reacting said acyclic conjugated dienes with said cyclopentadienes have the following formula (III):

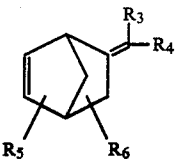

wherein $R_3$–$R_6$ are hydrogen or methyl.

The reaction according to the present invention is carried out in the presence of a catalyst composed of (A) a titanium-containing compound and (B) a metallic reducing agent.

For said titanium-containing compounds (A), compounds containing tetravalent or trivalent titanium are suitable, and cyclopentadienyltitanium halides having the following formula (I):

wherein X is chlorine, bromine or iodine, $R_1$ is hydrogen or $C_1$–$C_4$ alkyl group, m is 1 or 2, n is 2 or 3, and m+n =4; is preferable as the compounds containing tetravalent titanium.

Specific examples of cyclopentadienyltitanium halides include cyclopentadienyltitanium trichloride, cyclopentadienyltitanium tribromide, dicyclopentadienyl titanium dichloride, dicyclopentadienyltitanium dibromide and the like. In the cyclopentadienyltitanium halides of the above formula (I), particularly preferable is dicyclopentadienyltitanium dihalides such as dicyclopentadienyltitanium dichloride.

Preferable compounds containing tetravalent titanium other than those stated above are titanium-containing compounds having the following formula (II):

$$Ti(OR_2)_a (X)_{4-a} \qquad (II)$$

wherein X is halogen atom such as chlorine, bromine or iodine, $R_2$ is alkyl, aryl or aralkyl group containing 1–20 carbon atoms, and a is a number of $0 \leq a \leq 4$. Specific examples of the titanium-containing compounds of the above formula (II) include titanium tetrachloride, titanium tetrabromide, titanium tetraiodide, monomethoxytrichlorotitanium, dimethoxydichlorotitanium, trimethoxymonochlorotitanium, tetramethoxytitanium, monoethoxytrichlorotitanium, diethoxydichlorotitanium, triethoxymonochlorotitanium, tetraethoxytitanium, monoisopropoxytrichlorotitanium, diisopropoxydichlorotitanium, triisopropoxymonochlorotitanium, tetraisopropoxytitanium, monobutoxytrichlorotitanium, dibutoxydichlorotitanium, monopentoxytrichlorotitanium, monophenoxytrichlorotitanium, diphenoxydichlorotitanium, triphenoxymonochlorotitanium, tetraphenoxytitanium and the like.

On one hand, compounds containing trivalent titanium include titanium trihalides obtained by reducing titanium tetrahalides such as titanium tetrachloride, titanium tetrabromide and the like with hydrogen, aluminum, titanium or organic metallic compounds of the group I–III metals in the periodic table. In addition, there are other compounds containing trivalent titanium prepared by reducing tetravalent alkoxytitanium halides with organic metallic compounds of the group I–III metals in the periodic table.

In the present invention, the metallic reducing agents containing the group IA, IIA or IIIA metals in the periodic table (B) are used together with said titanium-containing compounds (A). These metals are, for example, lithium, sodium, potassium, rubidium, cesium, magnesium, calcium, vanadium, boron, aluminum, thallium and the like.

The metallic reducing agents (B) are specifically hydrides of metals (metal hydride) selected from the group IA, IIA or IIIA metals in the periodic table, and examples of which include $LiAlH_4$, (lithium aluminum hydride), $LiBH_4$, $LiAlH[OC(CH_3)_3]_3$, $LiAlH(OC_2H_5)_3$, $NaBH_4$ (sodium borohydride), $NaB(CN)H_3$, $(CH_3)_4NBH_4$, $(C_2H_5)_4NBH_4$, $BH_4$, $[(CH_3)_2CHCH(CH_3)]_2BH$, $NaAlH_4$ and the like. Among those, particularly preferable metal hydride is lithium aluminum hydride.

Other specific metallic reducing agents than the above-mentioned metal hydride include organic metallic compounds in which the metal is selected from sodium, lithium, aluminum, magnesium and thallium.

An example of organic sodium compounds is naphthyl sodium, cyclopentadienylsodium or the like.

Organic lithium compounds have the formula RLi wherein R is a $C_1-C_{20}$ alkyl, aryl or aralkyl group and examples of which include methyllithium, isobutyllithium and the like.

Organic aluminum compounds have the general formulae $(R)_3Al$, $(R)_2AlX$, $RAlX_2$, $(R)_2AlOR$, $RAl(OR)X$, and $(R)_2AlH$ (i.e. hydride) wherein each R is the same or different $C_1-C_{20}$ alkyl, aryl or aralkyl group, and X is halogen atom. Specific examples of these organic aluminum compounds include triethylaluminum, triisobutylaluminum, trihexylaluminum, trioctylaluminum, diethylaluminum chloride, diethylaluminum ethoxide, ethylaluminum sesquichloride, diethylaluminum hydride, dibutylaluminum hydride, diethylaluminum fluoride, diisobutylaluminum fluoride and the like.

Furthermore organic magnesium compounds have the formula RMgX wherein R is a $C_1-C_{20}$ alkyl, aryl or aralkyl group and X is halogen atom, and specific examples of which include, ethylmagnesium bromide ethylmagnesium chloride, methylmagnesium iodide, butylmagnesium chloride, cyclopentadienylmagnesium bromide and the like.

An example of organic thallium compounds is cyclopentadienylthallium or the like.

In the metallic reducing agents (B), one, two or more of the metals selected from the group IA, IIA or IIIA metals in the periodic table such as lithium, sodium, potassium, rubidium, cesium, magnesium, calcium, barium, strontium, aluminum and the like may be used. An alloy composed of two or more of these metals may also be employed. It is favorable to use these metals themselves in a state dispersed into an inert solvent. Particularly preferable metals are alkali metals such as lithium, sodium, potassium and the like.

A mixture obtained from two or more of the aforesaid metallic reducing agents in an arbitrary proportion may also be utilized.

Furthermore a halide of the group IIIA metals such as aluminum chloride and boron fluoride, or a metallic halide obtained from metals such as Zn, Fe, Zr and the like, for example, iron chloride, zinc chloride, zirconium chloride or the like may be used in combination with said metallic reducing agent in a suitable proportion. However, particularly preferable is that said halide is used together with a reducing agent consisting of alkali metal.

$10^{-4}-10^{-1}$ mol of the titanium-containing composed (A) per mol of cyclopentadienes is used in the present invention.

On one hand, 0.1–50 mol, and preferably 1–30 mol of the metal or metallic compound (B) per mol of the titanium-containin, compound (A) may be used in the process of the present invention.

Either the titanium-containing compound (A) may be introduced into reaction system separately from the metal or metallic compound (B), or both compounds (A) and (B) may have been admixed beforehand with an inert solvent, and then the admixture may be introduced into such reaction system. Usually it is desirable to use such admixture which has been prepared previously by admixing both the compounds with an inert solvent because of easy storage of catalyst, and easy handling in feeding of the compounds.

In the case of the reaction, conjugated dienes may be separately introduced into the reaction system from cyclopentadienes, but it is desirable in general that both compounds are simultaneously supplied to the reaction system. 0.05 –10 mol, and preferably 0.25 –2 mol of acyclic conjugated dienes are used per mol of cyclopentadienes. Succeedingly, said catalyst is introduced into the reaction system to commence the reaction.

The reaction according to the present invention may be effected in solvent-free condition, but preferable is to use such a solvent such as aromatic hydrocarbons, saturated aliphatic hydrocarbons and the like which are inactive with respect to the reaction. Specific examples of such solvent include benzene, alkylbenzenes such as toluene, xylene, mesitylene and the like, alkanes or cycloalkanes such as pentane, n-hexane, cyclohexane, n-octane, isooctane and the like. In addition, ethers such as ethyl ether, diglyme, dioxane, tetrahydrofuran and the like may also be used as the solvent as mentioned above.

A reaction temperature in the process of the present invention is within a range of 100°–300° C., and preferably 120°–250° C. When the reaction temperature exceeds 300° C., by-products having high boiling point, is produced easily, whilst yield of the product to be produced decreases at a temperature lower than 100° C., so that either case which is out of the aforesaid temperature range is not desirable.

Furthermore the reaction of the present invention can be carried out under dry atmosphere composed of an inert gas such as nitrogen, argon and the like, and the reaction pressure is not particularly limited in the reaction.

The reaction may be effected by either batch or continuous manner.

Reaction time is not especially limited in the present invention, but a reaction time of 10 minutes–10 hours is sufficient for carrying out the reaction in accordance with a batchwise manner of the process.

Thus, the alkylidenenorbornenes having the aforesaid formula (III) are obtained from acyclic conjugated dienes and cyclopentadienes. Examples of the alkylidenenorbornenes include isopropylidenenorbornene, ethylidenemethylnorbornene and the like in addition to the above-mentioned EBH.

The present invention can be advantageously applied to the case where EBH is particularly produced from BD and CPD or DCPD.

After completing the reaction, the catalyst is deactivated by either separating it from the reaction system by means of filtration or the like, or hydrolyzing the same, and then alkylidenenorbornenes are obtained through a suitable separating means such as vacuum distillation or the like.

The present invention will be described in detail in conjunction with the following examples.

EXAMPLE 1

(Run Nos. 1 –5).

Benzene (7 ml), CPD (40 mmol), and a catalytic amount of dicyclopentadienyltitanium dichloride which has been prepared in accordance with an ordinary method and lithium aluminum hydride were placed in a 50 ml autoclave, then liquefied and collected BD (80 mmol) was added thereto, and the resulting mixture was reacted in argon atmosphere for 3 hours at a temperature indicated in Table 1. In this reaction, a molar ratio of dicyclopentadienyltitanium dichloride: LiAlH$_4$CPD : BD was 1 : 4 : 150 : 300.

After completing the reaction, the catalyst was filtered out, and the reaction product was analyzed by means of gas chromatography. The results are shown in Table 1.

EXAMPLE 2

(Run No. 6)

An experiment was performed by the same manner as in Run No. 3 of Example 1 except that DCPD was used in place of CPD. The results are shown in Table 1 as in Example 1.

EXAMPLE 3

(Run No. 7)

The same experiment as in Run No. 1 in Example 1 was carried out except that a mixture of 0.81 mmol of lithium aluminum hydride and 0.55 mmol of sodium borohydride was used in place of lithium aluminum hydride catalyst, and the reaction was effected at 200° C. The results are shown in Table 1 as in the above Examples.

TABLE 1

| Run No. | Reaction Temperature °C. | Composition of Dimer (%) | | | | | | Yield[1] of EBH (%) |
|---|---|---|---|---|---|---|---|---|
| | | VCH [3] | VBH | EBH | THI [3] | DCPD | Others | |
| 1 | 140 | 12.3 | 3.2 | 27.5 | 4.6 | 38.5 | 13.4 | 14.5 |
| 2 | 160 | 17.8 | 6.8 | 32.8* | 5.0 | 24.8 | 12.8 | 30.3 |
| 3 | 180 | 14.6 | 7.6 | 43.8 | 14.9 | 6.2 | 12.9 | 34.8 |
| 4(*2) | 180 | 16.8 | 49.8 | — | 20.8 | 10.9 | 1.6 | — |
| 5 | 200 | 16.8 | 0.0 | 35.7 | 29.3 | 0.0 | 18.2 | 29.0 |
| 6 | 180 | 15.1 | 7.2 | 42.7 | 14.5 | 8.9 | 11.5 | 33.1 |
| 7 | 180 | 5.7 | 0 | 42.0 | 35.0 | 2.5 | 14.8 | 31.5 |

[1] Yield with respect to raw material CPD
(*2) For comparison, the experiment was effected with no catalyst. Yield of VBH was 30.6%.
[3] VCH: vinylcyclohexene THI: tetrahydroindene

EXAMPLE 4

(Run Nos. 8–18)

Benzene, CPD and BD as well as the titanium containing compounds (A) and the metals or metallic compounds (B) were placed in an autoclave with a ratio indicated in Table 2, respectively, and the mixture was then reacted in argon atmosphere at 180° C. for 3 hours. The results are shown in Table 2, respectively.

TABLE 2

| Run No. | Benzene (ml) | CPD (mmol) | BD (mmol) | Titanium-containing Compound (A) | (mmol) | Metal or Metallic Compound (B) | (mmol) | Yield of EBH (%) |
|---|---|---|---|---|---|---|---|---|
| 8 | 20 | 200 | 100 | Cyclopentadienyltitanium Trichloride | (1) | Lithium Aluminum Hydride | (2.5) | 30.1 |
| 9 | " | 400 | 200 | Dicyclopentadienyltitanium Dichloride | (0.5) | Diisobutylaluminum Hydride | (2.7) | 25.0 |
| 10 | " | " | " | Dicyclopentadienyltitanium Dichloride | (0.25) | Tri-n-octylaluminum | (2) | 30.0 |
| 11 | " | 200 | 100 | Titanium Trichloride | (4) | Lithium Aluminum Hydride | (5) | 29.7 |
| 12 | " | " | " | Titanium Trichloride | (2) | n-Btyllithium | (4) | 15.1 |
| 13 | 13.5 | " | " | Tetra-n-butoxytitanium | (0.5) | Lithium Aluminum Hydride | (2.5) | 32.4 |
| 14 | " | " | " | Tetra-iso-propoxytitanium | (0.5) | Diethylaluminum Hydride | (2.8) | 30.8 |
| 15 | " | " | | Tetra-iso-propoxytitanium | (0.5) | n-Butyllithium | (2.0) | 29.1 |
| 16 | 20 | " | " | Dicyclopentadienyltitanium Dichloride | (4) | Metallic Sodium | (22) | 28.6 |
| 17 | " | " | " | Titanium Tetrachloride | (1) | Aluminum Trichloride Metallic Sodium Cyclopentadienylthallium | (1.5) (20) (7) | 17.4 |
| 18 | 20 | 200 | 100 | Titanium Tetrachloride | (1) | Metallic Sodium Cyclopentadienylmagnesium Bromide | (5) (5) | 30.3 |

EXAMPLE 5

An experiment was performed by the same manner as in Run No. 3 of Example 1 except that methylcyclopentadiene was used in place of CPD.

The yield of methylethylidenenorbornene was 20.7%.

EXAMPLE 6

An experiment was performed by the same manner as in Run No. 3 of Example 1 except that piperylene was used in place of BD.

The yield of isopropylidenenorbornene was 10.8%.

What is claimed is:

1. A process for producing alkylidenenorbornenes by reacting $C_4$–$C_6$ acyclic conjugated dienes with cyclopentadiene, dicyclopentadiene, or a methyl- or dimethyl-substituted derivative thereof, in the presence of a catalyst composed of:
   (A) a titanium-containing compound, and
   (B) at least one metallic reducing agent containing a group IA, group IIA, or group IIIA metals in the periodic table.

2. A process for producing alkylidenenorbornenes as claimed in claim 1 wherein ethylidenenorbornene is produced from butadiene and cyclopentadiene or dicyclopentadiene.

3. A process for producing alkylidenenorbornenes as claimed in claim 1 wherein said titanium-containing compound

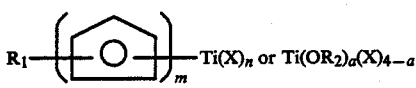

in which X is chlorine, bromine or iodine, $R_1$ is hydrogen or $C_1$–$C_4$ alkyl, m is 1 or 2, n is 2 or 3, m+n=4, $R_2$ is alkyl, aryl or aralkl containing 1 to 20 carbon atoms, and a is a number of $0 \leq a \leq 4$.

4. A process for producing alkylidenenorbornenes as claimed in claim 3 wherein said titanium-containing compound is cyclopentadienyltitanium halides having the following general formula (I):

     (I)

wherein X is chlorine, bromine or iodine, $R_1$ is hydrogen or $C_1$–$C_4$ alkyl group, m is 1 or 2, n is 2 or 3, and m+n=4.

5. A process for producing alkylidenenorbornenes as claimed in claim 3 wherein said titanium-containing compound is titanium trihalides or titanium compounds having the following formula (II):

     (II)

wherein X is halogen atom, $R_2$ is alkyl, aryl or aralkyl group containing 1-20 carbon aroms, and a is number of $0 \leq a \leq 4$.

6. A process for producing alkylidenenorbornenes as claimed in claim 3 wherein said metallic reducing agent is at least one agent selected from the group consisting of metal hydrides, organic sodium compounds, organic lithium compounds, organic aluminum compounds, organic magnesium compounds and organic thallium compounds.

7. A process for producing alkylidenenorbornenes as claimed in claim 6 wherein said metal hydride is lithium aluminum hydride.

8. A process for producing alkylidenenorbornenes as claimed in claim 6 wherein said metallic reducing agent is alkali metals.

9. A process for producing alkylidenenorbornenes as claimed in claim 6 wherein organic lithium compounds have the formula RLi wherein R is a $C_1$–$C_{20}$ alkyl, aryl or aralkyl group.

10. A process for producing alkylidenenorbornenes as claimed in claim 6 wherein said organic aluminum compounds have the formulae $(R)_3Al$, $(R)_2AlX$, $RAlX_2$, $(R)_2AlOR$, $RAl(OR)_x$ and $(R)_2AlH$ wherein each R is the same or different $C_1$–$C_{20}$ alkyl, aryl or aralkyl group and X is halogen atom.

11. A process for producing alkylidenenorbornenes as claimed in claim 6 wherein said organic magnesium compounds have a formula RMgX wherein R is a $C_1$–$C_{20}$ alkyl, aryl or aralkyl group and X is halogen atom.

12. A process for producing alkylidenenorbornenes as claimed in claim 6 wherein said organic sodium compound is naphthyl sodium or cyclopentadienylsodium.

13. A process for producing alkylidenenorbornenes as claimed in claim 6 wherein said organic thallium compound is cyclopentadienylthallium.

14. A process for producing alkylidenenorbornenes as claimed in claim 3 wherein the temperature of said reaction is within the range of 100 to 300 degrees C.

15. A process for producing alkylidenenorbornenes as claimed 3 wherein said reaction is conducted at a concentration of 0.0001 to 0.1 mol of said titanium-containing compound per mol of cyclopentadiene.

16. A process for producing alkylidenenorbornenes as claimed in claim 3 wherein said reaction is conducted at a concentration of 0.1 to 50 mols of said metallic reducing agent per mol of said titanium-containing compound.

17. A process for producing alkylidenenorbornenes as claimed in claim 16 wherein the temperature of said reaction is within the range of 100 to 300 degrees C and the concentration of said titanium-containing compound is 0.001 to 0.1 mol per mol of cyclopentadiene reactant.

18. A process for producing alkylidenenorbornenes as claimed in claim 17 wherein the concentration of acyclic conjugated diene is 0.05-10 mols per mol of cyclopentadiene reactant.

19. A process for producing alkylidenenorbornenes as claimed in claim 18 wherein the temperature of said reaction is within the range of 120 to 250 degrees C, the concentration of metallic reducing agent is 1 to 30 mols per mol of titanium-containing compound and the concentration of acyclic conjugated diene is 0.25 to 2 mols per mol of cyclopentadiene reactant.

20. A process for producing alkylidenenorbornenes as claimed in claim 19 wherein said catalyst comprises dicyclopentadienyl titanium dichloride and lithium aluminum hydride.

* * * * *